(12) United States Patent
Ermantraut et al.

(10) Patent No.: US 6,558,904 B2
(45) Date of Patent: *May 6, 2003

(54) METHOD FOR PRODUCING STRUCTURED, SELF-ORGANIZED MOLECULAR MONOLAYERS OF INDIVIDUAL MOLECULAR SPECIES, IN PARTICULAR SUBSTANCE LIBRARIES

(75) Inventors: Eugen Ermantraut, Jena (DE); Johann Michael Köhler, Golmsdorf (DE); Torsten Schulz, Jena (DE); Klaus Wohlfart, Laasan (DE); Stefan Wölfl, Jena (DE)

(73) Assignee: Clondiag Chip Technologies GmbH, Jena (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,443
(22) PCT Filed: Feb. 7, 1998
(86) PCT No.: PCT/EP98/00676

§ 371 (c)(1),
(2), (4) Date: Jul. 28, 1999

(87) PCT Pub. No.: WO98/36827

PCT Pub. Date: Aug. 27, 1998

(65) Prior Publication Data

US 2001/0049098 A1 Dec. 6, 2001

(30) Foreign Application Priority Data

Feb. 19, 1997 (DE) .......................... 197 06 570

(51) Int. Cl.$^7$ ............................ C12P 19/34; C07K 5/00
(52) U.S. Cl. ................. 435/6; 435/91.1; 435/DIG. 46; 435/DIG. 49; 536/25.3; 530/333; 530/334; 530/335
(58) Field of Search .................... 435/6, 91.1, DIG. 46, 435/DIG. 49; 536/25.3; 530/333–335

(56) References Cited

U.S. PATENT DOCUMENTS 4,199,649 A * 4/1980 Yundt .......................... 428/411
4,728,591 A * 3/1988 Clark et al. .................... 430/5
4,802,951 A * 2/1989 Clarke et al. ............... 156/630
4,868,096 A * 9/1989 Nakayama et al. ......... 430/329
5,258,091 A  11/1993 Imai et al. ................... 156/613
5,429,807 A   7/1995 Matson et al. .............. 422/131
5,489,678 A   2/1996 Fodor et al. ............... 536/22.1
5,599,695 A   2/1997 Pease et al. ............... 435/91.1
5,626,784 A * 5/1997 Simons ....................... 219/521
5,688,642 A * 11/1997 Chrisey et al. ................. 435/5

FOREIGN PATENT DOCUMENTS

WO    WO 97/06468    2/1997
WO    WO 97/33737    9/1997
WO    WO 98/27430    6/1998

OTHER PUBLICATIONS

Devries, German–English Science Dictionary (McGraw Hill) p. 6 1946.*
Kohler et al., Micromechanical Elements . . . , in Microsystem Technologies, Reichl and Heuberger (eds.), vde-Verlag, Berlin, 863–872 1994.*
Chrisey et al. Nucleic Acids Research vol. 24, No. 15 pp. 3040–3047 1996.*

* cited by examiner

Primary Examiner—Bennett Celsa
(74) Attorney, Agent, or Firm—Jordan and Hamburg LLP

(57) ABSTRACT

The invention relates to a method for producing structured, self-organized molecular monolayers of individual molecular species. The invention is preferably used to create solid-phase bonded substance libraries. To this end, a) a substrate (2) suitable for the first monolayer is provided; b) a microstructured polymer mask (1) having openings is applied to the subtrate (2) at least once in a defined direction. Said polymer mask (1) is sufficiently thin and flexible for it to adhere to the substrate (2) by adhesion, and the material selected for the polymer mask (1) is chemically stable; c) the sandwich constituted by the substrate (2) and polymer mask (1) is flooded with a first agent corresponding to the intended use, so as to create at least one first molecular monolayer in the areas defined by the mask openings; c1) depending on the monolayer structure to be created step c) is repeated using the first agent or one or more additional agents; and d) after carrying out the step described in c) or the steps described in c) and c1), the polymer mask is pulled off after modification of the substrate surface areas which were left uncovered by the mask openings and were subjected to the agent or agents.

4 Claims, 2 Drawing Sheets

Figure 1A:
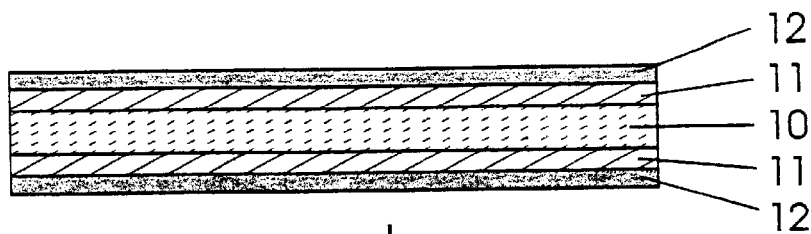

METHOD FOR PRODUCING STRUCTURED, SELF-ORGANIZED MOLECULAR MONOLAYERS OF INDIVIDUAL MOLECULAR SPECIES, IN PARTICULAR SUBSTANCE LIBRARIES

BACKGROUND OF THE INVENTION

This invention relates to a method for producing structured, self-organizing molecular monolayers of individual molecular species. The invention is preferably applied in the formation of solid phase-coupled substance libraries or in other assays for testing molecular interactions. Libraries of this kind which are used for fast detection of interacting reactants in the molecular field are known, in principle. Such substance libraries are generated in different ways according to the known prior art nearest to the invention. Thus, it is known to use so-called "microbeads"; i.e, small beads which are provided with a molecular reactant on their surface. Furthermore, a so-called "mix&split" procedure is known for producing such libraries (Erb, E.; Jander, K. D.; Brenner, S.: Recursive Deconvolution of Combinatorial Chemical Libraries, Proc. of Natl. Acad. Sci. USA 91, pg. 11422-6 (1994)). Solid phase-coupled libraries are particularly advantageous, the components of which are uniquely determined by their position (x-y-direction). For the serial production of such libraries modified jet printers are employed, for example, which by point-spraying apply the substances to be brought together on a preselected substrate (Schober, A. Guenther, R.; Schwienhorst, A. Doering, M.; Lindemann, B. F.: Accurate high-speed Liquid handling of very small biological samples, Biotechniques 15: pg. 324–9, 1993). So-called "applicators" have to be used for the parallel generation of such libraries, whereby a head being provided with a plurality of thin channels is set upon a surface, the head being adapted to simultaneously supply a plurality of micro-reaction cavities; refer, for example, to U.S. Pat. No. 5,429,807. Furthermore, to the same end, the application of light-activatable protective groups (U.S. Pat. No. 5,489,678) and of print-techniques has already been described (DE 195 43 232.0).

One or more basic disadvantage are inherent in these known methods and devices:

Thus the use of a jet-printer does not permit simultaneously supplying a greater number of surface elements with a substance all at once, since the process concerned is a serial one. The devices known as "applicators" are limited in to their technically feasibility with respect to the degree to which they can be miniaturized. The printing syntheses, which utilize prints having structurized and profiled surfaces for transferring substances, cause considerable problems with respect to an exact positioning; hence, reproducible multiple syntheses are practically excluded. Known methods of the complex protective group chemistry which use light-activatable protective groups require long exposure times when a high step efficiency is desired at, whereby the entire process for producing a library is rendered very time-consuming. Moreover, the light sensitivity of the last mentioned method necessitates a particularly expensive execution of the process. In Proc. Natl. Acad. Sci. USA, vol. 93, November 96, pg. 13555–13560 such a method for generating substance libraries is described in which at first a substrate is provided with a suitable protective group or with a monomer supporting a first protective group. Then a substrate surface is coated with a light-activatable photo-resist layer, and partial areas are exposed and structurized according to a preselected synthesis algorithm. In the structurized areas, the splitting-off of the protective group is carried out, then the bonding to a second polymer can be carried out in the exposed areas. After removal of the remaining photo-resist layers the entire process can be repeated with an accordingly adapted photo-resist layer which has to be structurized anew. The main disadvantage in this procedure is, apart from the disadvantages mentioned hereinbefore, the incomplete removal of the residues of the photo-resist layers from the library matrix, whereby the output per synthesis step and, hence, the entire synthesis output decreases.

SUMMARY OF THE INVENTION

It is an object of the present invention to provide a method for producing structured, self-organizing molecular monolayers of individual molecular species which permits the reproducible and multiple repeatability of the formation and locally defined bonding of molecular units to molecular monolayers, and ensures a high output. In particular, the method to is particularly intended for the production of test-assays and of solid-phase-bonded substance libraries.

According to the invention specially prepared micro-structurized polymeric masks are employed which are designed to be deposited upon a substrate and which, in preselected areas, are provided with apertures which permit the generation of monomolecular monolayers on the substrate.

DETAILED DESCRIPTION OF THE INVENTION

Figure 1B:
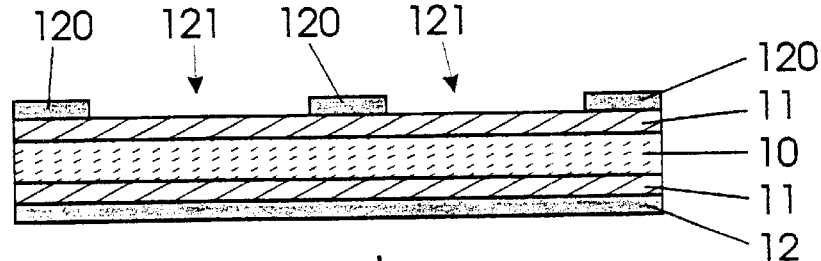
Figure 1C:
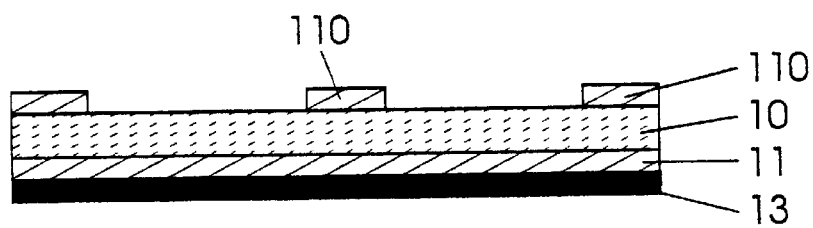
Figure 1D:
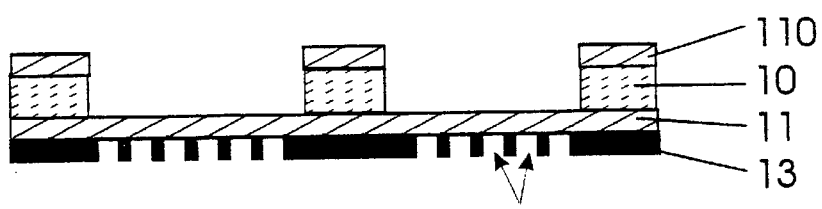
Figures 1E, 1F:
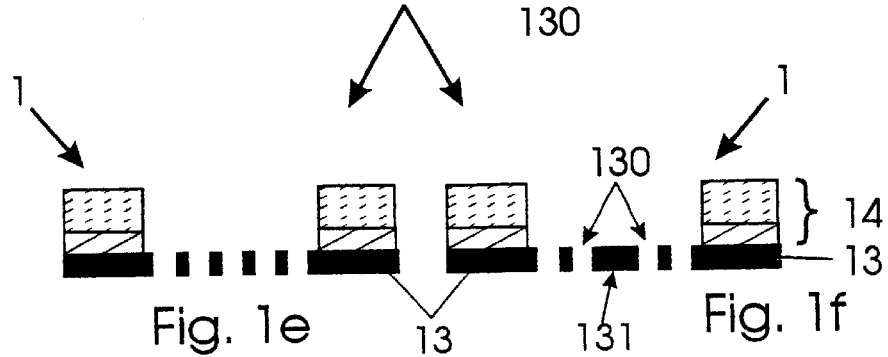
Figure 2:
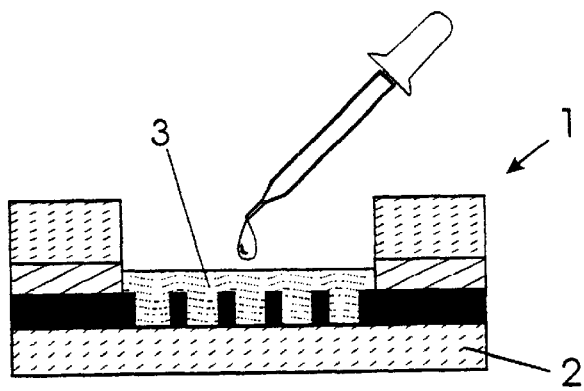
Figure 3:
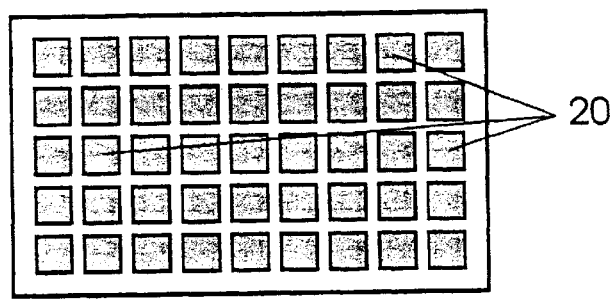

The invention will be explained hereinafter in more detail by reference to of embodiments schematically illustrated. There is shown in:

FIGS. 1*a* to 1*f* is a schematic representation of a procedure embodiment for producing the required polymeric masks, FIG. 2 is a schematic representation of a specific example of a procedure for producing a solid-phase-bonded substance library, FIG. 3 is an example of a surface nano-structurized in z-direction, in accordance with the invention.

Figure 4:
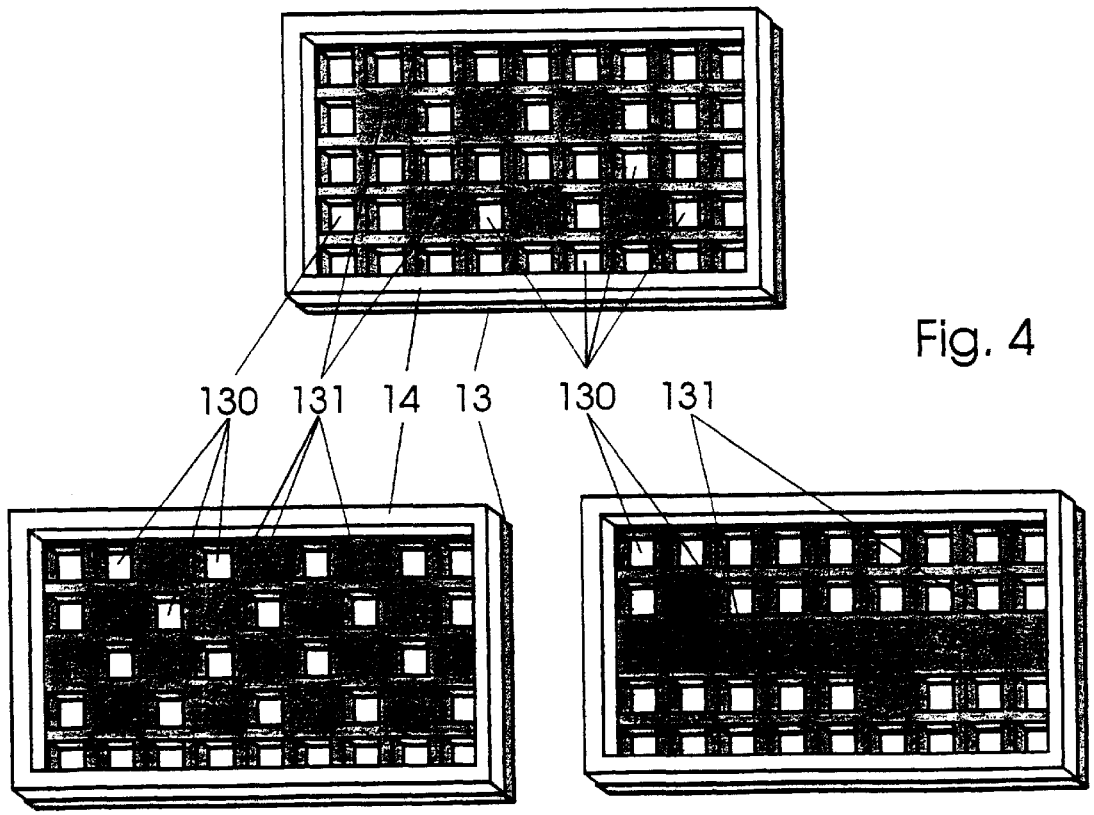

FIG. 4 shows a part, of a set of different polymeric masks for generating substance libraries.

In FIGS. 1*a* to 1*d* there is shown an example of an exemplary embodiment of a procedure for producing the polymeric masks required for the invention, wherein a 4" silicon wafer 10 shown in FIG. 1*a* is the starting point, the wafer being coated on each of its sides with a thermal $SiO_2$-oxide layer 11 of a thickness of 500 nm. The $SiO_2$-oxide layers 11 are covered with a photo-resist layer 12, as commonly used in micro-structuring, applied by spin-coating. One of the photo-resist layers 12 is provided with a not shown mask which is embodied in such a way that, as has to is hereinafter described, a frame 14 remains after completion of the polymeric mask structuring. The frame 14 is adapted in its dimensions to the substrate 2 which will be inserted later. The respective residual photo-resist layer areas 120 are shown in FIG. 1*b*, whereby windows 121 are formed. In accordance with the presetting by the mask, windows are etched into the first $SiO_2$-oxide layer 11 and the photo-resist layers are removed; the result of these steps, with the residual $SiO_2$-mask areas 110, is represented in FIG. 1*c*. Furthermore, FIG. 1*c* shows a newly deposited photo-structurable polymeric layer 13 which, in the example, is made of PDMS (polydimethylsiloxane) with addition of a crosslinking agent such as a diazido compound soluble in organic solvents, such as xylol or chloroform, or 2,2-dimethoxy-2-phenyl-acetophenone. It lies within the scope of the invention, also to use, depending on later cases of application and of the employed agents for this polymeric layer 13, other materials, for example, polyvinyl alcohol, PMMA, polyvinylpyrollidone etc., provided with a suitable crosslinking agent such as a salt of diazidostilbenesulfate. The polymeric layer 13 is provided with a further, not shown mask. The structure of the mask corresponds to those structures which by the structures to be generated in the polymeric layer 13 have later to be transmitted onto a substrate 2, still to be described. FIG. 1d shows the result of the structure generation in the polymeric layer 13 with the produced windows 130. At the same time FIG. 1d shows how the silicon areas that have not been covered by the $SiO_2$-mask areas 110, are removed by use of known etching means in a further processing step. Subsequently, the entire non-covered $SiO_2$-areas are removed in a further etching bath. In FIG. 1e there is shown the result of an individual silicon frame which is overlapped by a self-supporting, structured polymeric layer 13. This unit designated hereinafter as a micro-structured polymeric mask 1 has one or more applications within the scope of the invention. In order to produce substance libraries, further polymeric masks 1 of this kind are required, which hereinafter are all designated by the reference numeral 1. The predetermined windows 130 of the polymeric masks are principally designed congruently to one another. They are, however, adapted to a synthesis on modification algorithm by being partially constructed unopened, as schematically indicated in FIG. 1f by an arrow 131. The method of producing the structures in the polymeric layers 13 is irrelevant to scope of the invention; thus it is feasible to employ the so-called dry-etching procedures, when small openings up to the submicrometer range are required. It is essential only that the polymeric mask produced thin and flexible enough to hold onto a substrate 2, on which it has been deposited, by adhesion only, and that the mask is chemically stable towards agents which find application in the further procedure. Respective adjusting marks (not shown) are given to the entire polymeric masks 1 being used in the procedure and to the substrates 2 employed, the marks permitting a precise alignment, for example, by aid of mask-aligners conventionally used in micro-structuring.

In the following, the preparation of a substrate 2 according to the invention will be described by means an example illustrated in FIG. 2. A silicon wafer coated with gold is used as a substrate 2. The same should be freshly prepared and can be stored in double-distilled water. A polymeric mask 1 produced according to the foregoing example is superimposed upon the substrate 2 and is flooded with a reaction solution 3 which, by the way, is to react with the gold coat, which is not shown in more detail. In the example, NHS-SS-biotin dissolved to 10 $\mu$g/ml in phosphate buffer, 0.01 M, pH 8.5 is selected as reaction solution 3. After about 15 minutes incubation at room temperature, the surface is washed with pure buffer and distilled water and the polymeric mask 1 is pulled off. Subsequent thereto streptavidin is applied over the entire surface of the substrate 2, the streptavidin having an affinity of approximately $10^{-15}$ M binds to the biotin immobilized in the areas preselected by the opening areas 130 of the polymeric mask 1. Thus, the defined areas 20 are produced on the gold surface, only three of which are provided with reference lines in FIG. 3, which areas are exclusively occupied by streptavidin. It is feasible to employ a thus produced monomolecular mono-layer, which is subdivided into several, uniformly distributed areas 20, as, for example, an immobilizing matrix for biotinized molecules, but also as a substrate having a spatially selective adhesion or a defined boundary face energy.

In a further embodiment the preparation of a substrate is described which is adapted to serve as a parent substrate for the formation of a substance library. Herein, for example, a cleaned silicon wafer is used as a substrate 2, the entire surface of the same being, in the example, at first modified by treatment with 3-glycidoxypropyltrimethoxysilane. The substrate 2 is flooded by the 3-glycidoxypropyltrimethoxysilane (10% in toluene, 80° C., about 8 h). A two-hour incubation of the substrate in 0.05 M HCl leads to a hydrolysis of the mentioned epoxide, hence, there are free hydroxy-groups present. The latter spontaneously react, for example, with phosphoramidite. To this end, in the example, a C18 spacer-phosphoramidite, which is activated with 0.1M of tetrazole in solution in acetonitrile, reacts for 10 minutes with the modified substrate surface. Subsequently thereto the surface is washed thoroughly with acetonitrile. The surface of the substrate is now occupied by dimethoxytrityl-groups, the latter being known standard protective groups in the chemistry of phosphoramidite protective groups.

A polymeric mask 1, produced, for example, according to FIG. 1 is deposited upon the substrate 2, prepared analogously to the procedure described with reference to FIG. 2, and positioned by means of a mask-aligner. After positioning, the sandwich arrangement, constituted of the substrate 2 and of the polymeric mask 1, can be taken from the holder, since the polymeric mask, due to its design, sticks by adhesion to the surface of the substrate. 2% trifluoroacetic acid in $H_2O$ is applied over the sandwich arrangement, wherein a splitting-off of the protective groups, produced in accordance with the above example, takes place in the windows 130 of the polymeric masks. Subsequently, the polymeric mask 1 is pulled off the substrate and areas 20, distributed as in analogy FIG. 3, are obtained which are freed from a predefinedly selected protective group. The substrate can be used as test-assay already in this state. The specific kind of preparation of the substrate varies and can be adapted to a great number of later applications. The substrate prepared in such a way can subsequently be subjected, for example, to a phosphoramidite cycle as generally known, in order to add a further oligonucleotide-monomer to the designated areas 20 by synthesizing.

In order to set up a substance library further polymeric masks 1 are provided according to the invention which, in accordance with the substance group to be synthesized, have to be variably and adaptably embodied in such a manner that the openings 130 in principle congruently correspond to the openings 130 of the first polymeric mask. However, the former have some unopened mask areas 131, as indicated by example of FIG. 4. It also lies within the scope of the invention to provide for larger openings, if required, so that adjacent larger areas on the substrate can be treated. In order to augment the molecular species at the particular location, a new polymeric mask, which corresponds to the synthesis cycle, is superimposed, the substance to be synthesized is deposited, the respective reaction and cleaning steps are carried out, and finally the polymeric mask employed is pulled off. In spite of the thereby resulting different growth of height of the individual molecular species, constituted of a plurality of monomers each, in the different synthesis areas of the substrate, the adhesive sticking of the respective polymeric masks is maintained, and even with synthesized layer stacks of chain lengths of 30–100 or more, there will be no underwashing of the respective polymeric masks by the subsequent synthesis solution. In the manner described it is feasible to reliably set up substance libraries of high reproducibility and output, with the aid of apparatus techniques from the field of microstructuring.

It is feasible to set-up any desired polymeric and substance libraries such as, for example, peptide, polysaccharide, polyterpene etc. libraries by means of the present invention. It is also feasible to produce mixed libraries, which is to be understood as the application of molecular species from different substance classes on a substrate. Furthermore, there is the feasibility of setting-up libraries with mixed polymers which means polymers consisting of monomers from different substance classes. This, however, requires the compatibility of the protective groups and of the functional coupling groups. The production of branched polymers by use of respective multiply functionalized and multiply-protected monomers is also feasible.

The described problems in the substance libraries produced according to the prior art are effectively obviated. The openings provided in the employed polymeric masks can be produced up into the submicrometer range. The method of the invention offers the basic advantage of in no way restricting the respective chemistry applied. The materials of the employed mechanical parts are generally adaptable to the reaction cycle.

What is claimed is:

1. A method for producing structured, self-organizing molecular monolayers of individual molecular species, comprising preparing a partially masked substrate by applying to a uniformly flat substrate a mask comprising a polymeric film which is sufficiently thin and flexible that it adheres to the substrate only by adhesion, the polymer of the mask being selected from the group consisting of cross-linked polydimethylsiloxane cross-linked polyvinyl alcohol, cross-linked polymethyl methacrylate and cross-linked polyvinyl pyrollidone and being chemically stable with respect to any chemical reagent used in a subsequent step of the method, the polymeric film having fabricated openings corresponding to areas of the substrate to which reagents are to be applied;

at least one step of applying a reagent onto the partially masked substrate thereby to form a first molecular monolayer only on areas of the substrate corresponding to the fabricated openings in the polymeric film; and pulling off the mask, the pulled off mask being reusable.

2. A method according to claim 1, comprising at least one additional step of applying to said substrate from which the mask previously applied thereto has been pulled off an additional mask comprising an additional polymeric film which is sufficiently thin and flexible that it adheres to the substrate only by adhesion, the polymer of the additional mask being selected from the group consisting of cross-linked polydimethylsiloxane, cross-linked polyvinyl alcohol, cross-linked polymethyl methacrylate and cross-linked polyvinyl pyrollidone and being chemically stable with respect to any chemical reagent used in a subsequent step of the method, the additional polymeric film having prefabricated openings corresponding to prefabricated openings in the previous polymeric film but also having some at least partially unopened areas corresponding to prefabricated openings in the previous polymeric film.

3. A method according to claim 1 or 2, in which each mask comprises a respective frame integral with the respective polymeric film and having exterior dimensions substantially corresponding to the exterior dimensions of the substrate, the prefabricated openings in each respective polymeric film being located in areas of the respective polymeric film circumscribed by the interior edges of the respective frame.

4. A method according to claim 3, in which the periphery of each respective polymeric film substantially coincides with the exterior periphery of the respective frame.

* * * * *